United States Patent
Tanaka et al.

(10) Patent No.: US 7,383,511 B2
(45) Date of Patent: Jun. 3, 2008

(54) SYSTEM, METHOD AND RECORDING MEDIUM FOR MEDICAL IMAGE MANAGEMENT

(75) Inventors: Hiroshi Tanaka, Kaisei-machi (JP); Kazuo Shimura, Kaisei-machi (JP); Takeshi Ohkubo, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 09/910,836

(22) Filed: Jul. 24, 2001

(65) Prior Publication Data
US 2002/0019832 A1    Feb. 14, 2002

(30) Foreign Application Priority Data
Jul. 24, 2000   (JP)   ............... 2000-221630

(51) Int. Cl.
*G06F 3/00* (2006.01)
*A61B 5/00* (2006.01)

(52) U.S. Cl. .............. 715/748; 715/733; 715/700; 600/300

(58) Field of Classification Search .............. 715/530, 715/748, 543–544, 751, 733, 512; 382/128, 382/132; 707/10, 102, 104, 104.1; 600/300, 600/407, 410, 425
See application file for complete search history.

(56) References Cited

U.S. PATENT DOCUMENTS

| | | | | |
|---|---|---|---|---|
| 5,655,084 A | * | 8/1997 | Pinsky et al. | 705/3 |
| 5,754,704 A | * | 5/1998 | Barnsley et al. | 382/249 |
| 6,269,379 B1 | * | 7/2001 | Hiyama et al. | 707/104.1 |
| 6,349,373 B2 | * | 2/2002 | Sitka et al. | 711/161 |
| 6,381,029 B1 | * | 4/2002 | Tipirneni | 358/1.14 |
| 6,418,475 B1 | * | 7/2002 | Fuchs | 709/238 |
| 6,434,569 B1 | * | 8/2002 | Toshimitsu et al. | 707/100 |
| 6,598,011 B1 | * | 7/2003 | Howards Koritzinsky et al. | 702/185 |
| 6,603,494 B1 | * | 8/2003 | Banks et al. | 345/807 |
| 6,608,628 B1 | * | 8/2003 | Ross et al. | 345/619 |
| 6,847,933 B1 | * | 1/2005 | Hastings | 600/437 X |
| 6,947,581 B1 | * | 9/2005 | Patel et al. | 707/10 X |
| 2002/0007287 A1 | * | 1/2002 | Straube et al. | 707/10 X |
| 2003/0105393 A1 | * | 6/2003 | Sutherland et al. | 600/407 |
| 2005/0154288 A1 | * | 7/2005 | Wang et al. | 600/407 |

* cited by examiner

Primary Examiner—Sy D. Luu
(74) Attorney, Agent, or Firm—Sughrue Mion, PLLC

(57) ABSTRACT

In a small-scale medical facility, appropriate storage and management of medical images whose storage is mandatory for a predetermined period becomes easier. A storage terminal installed in a medical facility is connected to a mobile storage system, and image data stored in the storage terminal are transferred to the mobile storage system. The mobile storage system storing the image data is connected to an image data storage apparatus installed in an image storage center, and transmits the image data to the image data storage apparatus. The image data storage apparatus stores the image data and calculates the date of storage expiration of the image data. The image data storage apparatus stores the image data until the expiration date.

31 Claims, 4 Drawing Sheets

| | ACCOMPANYING INFORMATION | | | | | RECEPTION INFORMATION | |
|---|---|---|---|---|---|---|---|
| IMAGE NUMBER | FACILITY | PATIENT ID | INPUT MODALITY | DATE OF PHOTOGRAPHING | ... | DATE OF RECEPTION | ... |
| AF12345 | A223 | 671231 | CR | 00/03/18 | | 00/04/13 | |
| AA23456 | A233 | 100811 | CT | 00/03/20 | | 00/04/13 | |
| AA34567 | A233 | 101562 | CT | 00/03/21 | | 00/04/13 | |
| ⋮ | ⋮ | ⋮ | ⋮ | ⋮ | | ⋮ | |
| AE45678 | F124 | 554800 | CR | 00/04/18 | | 00/04/20 | |

FIG. 3

| IMAGE NUMBER | FACILITY | PATIENT ID | INPUT MODALITY | DATE OF PHOTOGRAPHING | ... | DATE OF RECEPTION | ... |
|---|---|---|---|---|---|---|---|
| AF12345 | A223 | 671231 | CR | 00/03/18 | | 00/04/13 | |
| AA23456 | A233 | 100811 | CT | 00/03/20 | | 00/04/13 | |
| AA34567 | A233 | 101562 | CT | 00/03/21 | ... | 00/04/13 | |
| ......... | | | | | | | |
| AE45678 | F124 | 554800 | CR | 00/04/18 | | 00/04/20 | |

{ ACCOMPANYING INFORMATION } { RECEPTION INFORMATION }

SYSTEM, METHOD AND RECORDING MEDIUM FOR MEDICAL IMAGE MANAGEMENT

BACKGROUND OF THE INVENTION

1. Field of the Invention

The present invention relates to a medical image management system for managing medical image data. More specifically, the present invention relates to a medical image management system for managing medical image data owned by medical facilities but situated outside the medical facilities.

2. Description of the Related Art

In medical facilities such as clinics and hospitals, a large number of medical images such as X-ray images, CT images, and MR images have been in wide use. Medical facilities store such medical images in order to understand changes in patients' conditions. Furthermore, medical facilities store such medical images for a long time, since storage of medical images of some types is mandatory for a predetermined period. Such medical images have been conventionally stored in the form of hard copies.

However, since medical images are photographed upon necessity at the time of medical treatment in medical facilities, medical images such as X-ray films are continuously increasing in number. In order to store X-ray films in a preferable condition for a long time, the X-ray films need to be stored in isolation from moisture and light. Therefore, measures for the isolation are also necessary. Recently, there has been proposed a medical image filing apparatus for storing (filing) medical images after digitization thereof in the form of image data sets in a recording medium such as a magneto-optic disc and for enabling searches for a desired one of the image data sets.

When the medical image filing apparatus is used, storage space for X-ray films or the like in a medical facility can be substantially saved. Moreover, a desired one of the image data sets can be searched for among the image data sets, and outputting the image data on a film is also possible if necessary. Therefore, storage of medical images by digitization of the images (hereinafter called electronic storage) has been put into practice in medical facilities.

Meanwhile, storage of medical images of some types is mandatory, and medical facilities have responsibilities for electronic storage of data representing images whose storage is mandatory.

For example, a medical facility carrying out electronic storage bears accountability. That is, the medical facility explains to a third party that an apparatus, a system and the like for electronic storage installed in the facility (hereinafter called the electronic storage system) satisfy a predetermined standard. The "predetermined standard" refers to a standard for securing safety and reproducibility of medical image data that are stored in the system, for example. Furthermore, a medical facility carrying out electronic storage also accepts managerial responsibility for managing the electronic storage system, and liability for a problem or loss caused by the electronic storage system. In addition to those responsibilities described above, a medical facility is responsible for restoring the image data in the electronic storage system in the case of destruction, for example.

In the case where a medical facility having only one doctor carries out electronic storage, the doctor should appropriately manage all image data as a target of the mandatory storage Since this management is a far cry from carrying out actual medical treatment, such a doctor and a medical facility originally aimed at medical treatment are burdened with this management. Furthermore, doctors are burdened more with management of a storage period and ensuring there is no accidental deletion of medical image whose storage is mandatory.

SUMMARY OF THE INVENTION

The present invention has been conceived based on consideration of the problems described above. An object of the present invention is therefore to provide a medical image management system for enabling reduction of a burden of electronic storage of medical images on the only doctor in a small-scale medical facility, for enabling management of medical image data, and for enabling storage of medical images whose storage is mandatory for a predetermined period without involving the only doctor. The present invention also provides a computer-readable recording medium used for the medical image management system.

A medical image management system of the present invention comprises:

a mobile image data reception device connectable to medical image data storage means installed in a medical facility and having a function of receiving medical image data sets stored in the medical image data storage means from the medical image data storage means and having a function of storing the medical image data sets; and an image data storage apparatus connectable to the mobile image data reception device and having a function of receiving the medical image data sets transmitted from the mobile image data reception device and a function of storing the image data sets. The medical image management system is characterized by the fact that the image data storage apparatus comprises storage period management means for managing a storage period of each of the medical image data sets stored therein.

The "medical image data storage means" refers to any recording medium enabling storage of the image data sets, such as a hard disc and a magneto-optic disc.

It is preferable for the mobile image data reception device to further have a function of transmitting a reception completion signal to the medical image data storage means at the time of reception completion of the medical image data sets. In other words, it is preferable for the medical facility to be notified of reception of the medical image data sets when the mobile image data reception device receives the medical image data sets from the medical image data storage means. Various methods of indicating the reception completion, such as adding information indicating reception completion to the medical image data sets stored in the medical image data storage means in the medical facility, can be used in addition to the transmission of the reception completion signal described above.

The mobile image data reception device used in the medical image management system of the present invention is connectable to the medical image data storage means installed in the medical facility and has the function of receiving the medical image data sets stored in the medical image data storage means and having the function of storing the medical image data sets.

The image data storage apparatus used in the medical image management system of the present invention is connectable to the mobile image data reception device having the function of receiving the medical image data sets transmitted from the mobile image data reception device, and has the function of storing the medical image data sets. The image data storage apparatus comprises the storage period management means for managing the storage period of each of the medical image data sets that have been stored.

Another aspect of the medical image management system of the present invention comprises medical image data storage means installed in a medical facility for storing and transmitting medical image data sets, and an image data storage apparatus for enabling reception of the medical image data sets from the medical image data storage means and for storing the medical image data sets. The medical image management system is characterized by the fact that the image data storage apparatus comprises storage period management means for managing a storage period of each of the medical image data sets stored therein.

It is preferable for the image data storage apparatus to comprise means for regularly measuring a total amount of the medical image data sets stored in the medical image data storage means, for calculating a difference between a capacity of the medical image data storage means and the total amount of the medical image data sets, and for receiving the medical image data sets from the medical image data storage means when the difference becomes smaller than a predetermined value.

The "predetermined value" is a value corresponding to an amount of image data representing one medical image, for example. In other words, the predetermined value is a value determined for receiving the medical image data sets from the medical image data storage means before the total amount of the medical image data sets stored in the storage means exceeds the capacity of the storage means.

Meanwhile, the medical image data storage means may have a function of transmitting a reception request signal for requesting reception of the medical image data sets stored in the medical image data storage means. In this case, the image data storage apparatus has a function of receiving the reception request signal. In other words, the medical facility may request reception of the medical image data sets by the image storage apparatus regularly or upon necessity such as the case where important image data need to be stored, or before a long closure of the medical facility or replacement of the medical image data storage means.

The medical image data storage means may regularly measure the total amount of the medical image data sets stored therein and calculate the difference between the capacity and the total amount of the medical image data sets so that the medical image data storage means can transmit the reception request signal when the difference becomes smaller than the predetermined value.

Furthermore, it is preferable for the image data storage apparatus to have a function of transmitting a storage completion signal to the medical image data storage means at the time of storing the medical image data sets.

The medical image data storage means used in the medical image management system of the present invention is installed in the medical facility. The medical image data storage means stores the medical image data sets, and enables transmission of the medical image data sets.

The image data storage apparatus used in the medical image management system of the present invention stores the medical image data sets received from the medical image data storage means, and may comprise storage period management means for managing the storage period of each of the medical image data sets.

It is preferable for the image data storage apparatus to further comprise output means for outputting a desired one of the medical image data sets stored therein according to a predetermined output condition input thereto.

A program to cause a computer in the mobile image data reception device used in the medical image management system of the present invention to execute processing may be provided by being recorded in a computer-readable recording medium. The program comprises the procedures of:

receiving the medical image data sets stored in the medical image data storage means installed in the medical facility from the medical image data storage means and storing the image data sets; and transmitting the medical image data sets that have been received and stored to the image data storage apparatus.

Furthermore, a program to cause a computer in the image data storage apparatus used in the medical image management system of the present invention to execute processing may be provided by being recorded in a computer-readable recording medium. The program comprises the procedures of:

receiving the medical image data sets from the mobile image data reception device; and managing the storage period of each of the medical image data sets that have been stored.

Moreover, a program to cause the computer in the image data storage apparatus used in the medical image management system of the present invention to execute processing may be provided by being recorded in a computer-readable recording medium. The program comprises the procedures of:

regularly measuring the total amount of the medical image data sets stored in the medical image data storage means;

calculating the difference between the capacity of the storage means and the total amount of the medical image data sets in the medical image data storage means; and receiving the medical image data sets from the medical image data storage means when the difference becomes smaller than the predetermined value.

Each of the medical image data sets includes not only data of a medical image but also accompanying information regarding the medical image data set, such as facility information, patient identification information, image identification information, and information of the data of photographing and an input modality. The patient identification information refers to information for identifying a patient, such as a patient ID and the name of the patient. The image identification information refers to information such as an image number for identifying each of the image data sets. It is preferable for the image identification information to include information indicating whether or not each of the image data sets is to be stored in the image data storage apparatus. In other words, the image number of the image data sets to be stored in the image data storage apparatus starts with "A" and otherwise, the image number starts with "B", for example.

The "reception" of the medical image data sets from the medical medical image data storage means refers to reception of the medical image data sets transmitted from the storage means or acquisition of the medical image data sets stored in the storage means by accessing the storage means.

The storage period management means in the image data storage apparatus refers to functions of referring to the date of photographing in the accompanying information of each of the medical image data sets that have been received, calculating the date of storage expiration by using the date of photographing and a mandatory storage period of the medical image data set, and storing the medical image data set in the image data storage apparatus until the expiration date. The mandatory storage period is determined for each type of the medical image data. The storage period maybe recorded as the accompanying information of each of the medical image data sets by the medical facility. Alternatively, the image storage apparatus may judge the storage period by using the accompanying information such as the input modality, for example. The date of photographing used as a reference for calculating the storage expiration date can be replaced by the date of reception of each of the medical image data sets from the storage means. In other words, any method for calculating the expiration date can be used as long as each of the medical image data sets can be securely stored at least for the mandatory storage period.

A medical image management method of the present invention comprises the steps of:

storing medical image data sets in storage means installed in a medical facility;

receiving the medical image data sets from the storage means by an image data storage apparatus installed outside the medical facility and storing the image data sets; and managing a storage period of each of the medical image data sets that have been stored.

According to the medical image management system of the present invention having the above configuration, each of the data sets of the medical image whose storage is mandatory is securely stored in the image data storage apparatus outside the medical facility in the mandatory storage period. Therefore, without management of the storage period and a storage state by the doctor, the image data sets can be stored and managed appropriately. As a result, the image data storage apparatus outside the medical facility can take on a portion of the managerial responsibility for management of the electronic storage system and liability for a loss or the like caused by the system, which reduces a burden on the doctor.

In the case where the image data storage apparatus storing the image data sets further comprises the output means, reproducibility of the image data sets is secured. Therefore, the medical facility can fulfill the accountability to a third party that assures the security and the reproducibility of the image data sets.

In the case where the mobile image data reception device or the image data storage apparatus has the function of notifying the medical facility of storage of the medical image data sets at the time of reception or storage of the image data sets, the medical facility becomes aware of reception or storage of the medical image data sets. In this manner, the image data sets stored in the medical image data storage means can be easily deleted and managed, for example.

If the medical facility deletes the medical image data sets that have been stored in the image data storage apparatus from the medical image data storage means, and stores only the medical image data sets that are constantly accessed, the medical facility only has to store the image data sets having a constant amount, which leads to easier management.

If the medical facility keeps the image data sets that have been stored in the image data storage apparatus without deleting the image data sets, the image data sets are stored at two locations. Therefore, a responsibility for security of the image data sets, such as restorability of the image data sets in the case of destruction, can be fulfilled.

BRIEF DESCRIPTION OF THE DRAWINGS

FIG. 3 shows an example of accompanying information and reception information used in the medical image management system in the embodiment.

DESCRIPTION OF THE PREFERRED EMBODIMENTS

Figure 1:
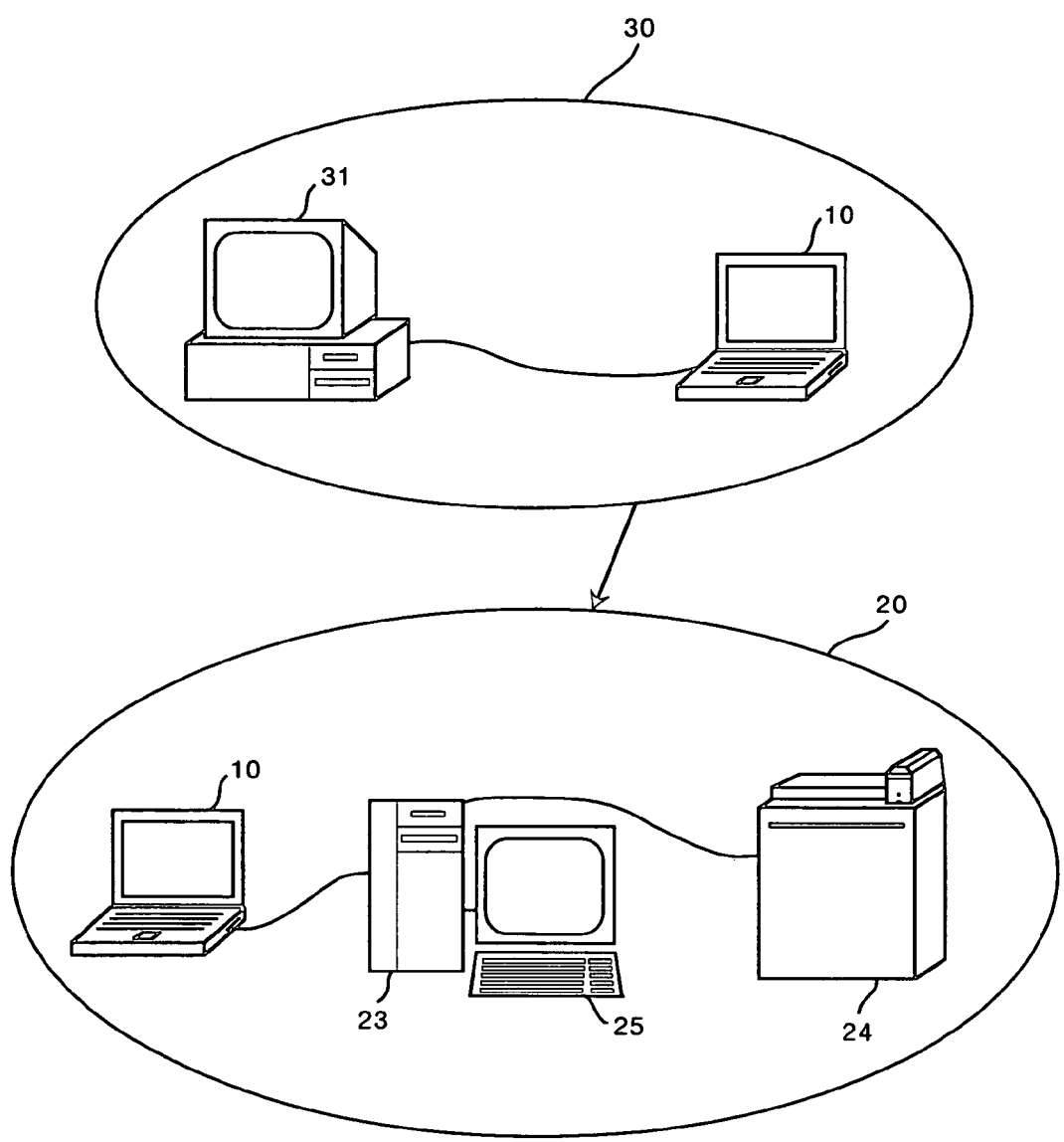
FIG. 1 is a diagram showing a configuration of a medical image management system as an embodiment of the present invention.

Hereinafter, embodiments of a medical image management system of the present invention will be explained with reference to the accompanying drawings. FIG. 1 is a diagram showing a configuration of a first embodiment of the medical image management system of the present invention.

A medical image management system in this embodiment comprises a mobile storage system 10 for receiving image data sets and connectable to a storage terminal 31 installed in a medical facility 30, and an image data storage apparatus 23 installed in an image data storage center 20.

The medical facility 30 has the storage terminal 31 having a built-in hard disc for data storage. The storage terminal 31 comprises an input/output terminal for inputting/outputting the image data sets and accompanying information on the image data sets. The hard disc of the storage terminal 31 stores the image data sets generated by digitization of medical images such as CR images, X-ray film digitized images, CT images, and MR images photographed in the medical facility 30 and the accompanying information of the image data sets. As shown in FIG. 3, the accompanying information refers to facility information, patient identification information such as a patient ID, image identification information such as an image number, and information on an input modality and the date of photographing, for example.

The mobile storage system 10 comprises an input/output terminal for inputting/outputting the image data sets and the accompanying information (hereinafter simply called the image data sets and the like), and the hard disc for storing the image data sets and the like. The mobile storage system 10 may have a recording medium storing a program for reception and transmission of the image data sets and the like and a program for recording reception information such as the date of reception and a name of a data reception operator at the time of receiving the image data sets and the like.

Figure 2:
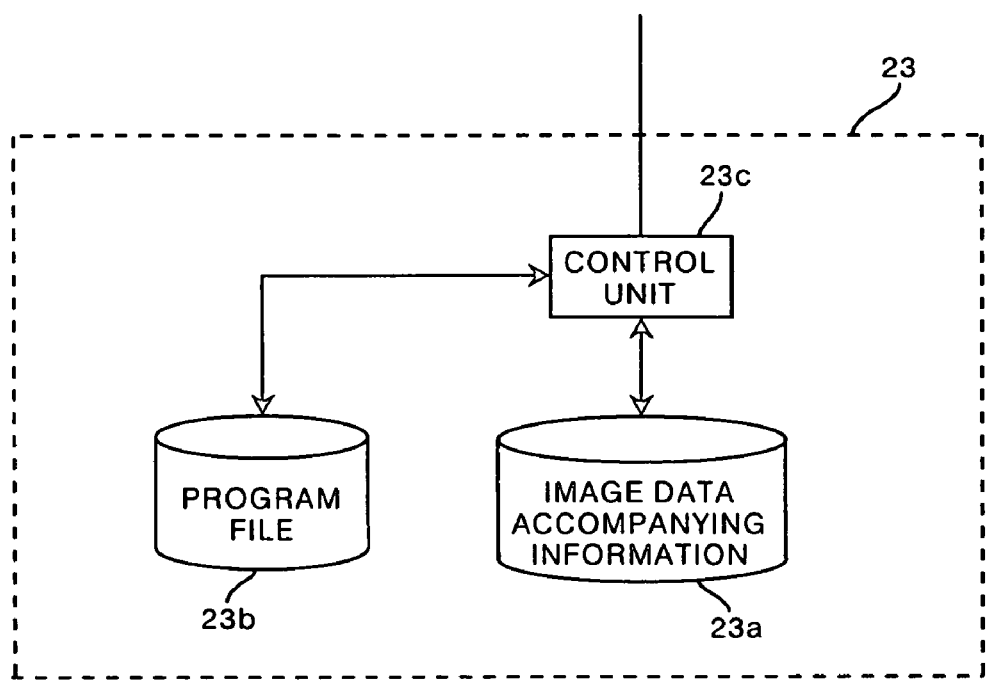
FIG. 2 is a diagram showing a configuration of an image data storage apparatus in the embodiment.

The image data storage apparatus 23 is connectable to the mobile storage system 10 in a state where transmission and reception of the image data sets and the like and the reception information is possible therebetween. The image data storage apparatus 23 stores and manages the image data sets and the like and the reception information transmitted from the mobile storage system 10. More specifically, as shown in FIG. 2, the image data storage apparatus 23 comprises a data storage unit 23a for storing the image data sets and the like, a program storage unit 23b for storing various kinds of programs, and a control unit 23c for controlling execution of the programs, data input/output, and the like. The data storage unit 23a stores the image data sets and the like and the reception information transmitted from the mobile storage system 10 via the control unit 23c. The program storage unit 23b stores a program for searching for a desired one of the image data sets stored in the data storage unit 23a, a program for displaying a screen on an input device 25, a program for calculating the date of storage expiration of each of the image data sets in the data storage unit 23a, for example. The control unit 23c has a function of executing the programs stored in the program storage unit 23b, and a function of controlling input/output or the like of the image data sets and the like stored or to be stored in the data storage unit 23a.

The input device 25 is connected to the image data storage apparatus 23. A menu screen enabling selection of reception, search, output, management and the like of the image data sets is displayed on the screen of the input device. A keyboard comprising the input device 25 is used for transmitting various kinds of instructions to the image data storage apparatus 23.

A printing apparatus 24 is connected to the image data storage apparatus 23, and has a function of printing an image by outputting the corresponding image data set transmitted from the image data storage apparatus 23 on an X-ray film or the like.

Operation of the medical image management system in this embodiment having the above configuration will be explained next.

The medical facility 30 photographs the medical images such as X-ray images, CT images, and MR images for medical treatment upon necessity, and stores the images in the hard disc of the storage terminal 31 in the form of the image data sets. The accompanying information on the image data sets is also stored in the hard disc of the storage terminal 31 together with the image data sets.

The data reception operator in the image storage center 20 visits the medical facility 30 regularly or on request, and receives the image data sets and the like having a predetermined amount agreed by the medical facility from the hard disc of the storage terminal 31 to the mobile storage system 10 of the operator by connecting the system 10 to the terminal 31. The mobile storage system 10 records the reception information comprising the date of reception and the name of the data reception operator, and stores the reception information together with the image data sets and the like.

The data reception operator brings the mobile storage system 10 having the image data sets and the like therein to the image storage center 20, and connects the mobile storage system 10 to the image data storage apparatus 23 installed in the image storage center 20. The data reception operator selects data reception from the menu screen displayed on the input device 25 and carries out data reception by using the image data storage apparatus 23. The image data sets and the like and the reception information stored in the hard disc of the mobile storage system 10 are then received by the image data storage apparatus 23, and stored in the data storage unit 23a of the image data storage apparatus 23.

After the medical facility 30 confirms that the image data sets received by the mobile storage system 10 are securely stored in the image storage center 20, the image data sets stored in the storage terminal 31 are deleted at the discretion of the medical facility 30. In other words, since it is convenient for images frequently used in the facility to be kept in the medical facility even if the data sets of the images have been stored in the image storage center 20, the medical facility 30 selects a portion of the image data sets to be deleted from the hard disc of the storage terminal 31 from the image data sets that have been stored in the image storage center 20, and deletes the selected portion of the image data sets.

When the medical facility 30 needs a portion of the image data sets stored in the image storage center 20 for transfer of a patient or the like, an output request is sent to the image storage center. A management operator in the image storage center 20 receiving the output request carries out output processing on the requested portion of the image data sets. In other words, the management operator inputs a search condition used for the requested portion of the image data sets, such as the facility information and the patient ID included in the accompanying information by using the input device 25. The control 23c of the image data storage apparatus 23 searches the image data sets stored in the data storage unit 23a for the requested portion of the image data sets and transmits the requested portion of the image data sets to the printing apparatus 24. The printing apparatus 24 outputs the portion of the image data sets that has been received on an X-ray file or the like. A company managing the image storage center 20 provides various kinds of services including the output request service each having a different charge. For example, a charge may be changed depending on frequency of reception of the image data sets from the storage terminal 31 installed in the medical facility 30 by the mobile storage system 10. The medical facility 30 can select a desired one of the services depending on urgency and budget. Furthermore, the company may provide a service of delivering a portion of the image data sets stored in the image storage center 20 to a pertinent facility specified by the medical facility 30 or to a patient, for example.

The image storage center 20 manages the storage expiration date of each of the image data sets stored in the image data storage apparatus 23. In other words, the image data storage apparatus 23 calculates the storage expiration date by using the date of reception of each of the image data sets included in the reception information or the date of photographing included in the accompanying information stored in the data storage unit 23a, and a mandatory storage period of each of the image data sets. The mandatory storage period is determined in advance for each type of medical image data, and the image data storage apparatus 23 judges the mandatory storage period by using the accompanying information of each of the image data sets received by the apparatus. After the expiration date for one of the image data sets has passed, the management operator of the image storage center 20 deletes the image data set that has expired, based on a contract between the company and the medical facility 30. The exact nature of deletion processing is determined individually according to the contract with the medical facility 30. For example, the medical facility 30 can select processing such as "deletion of the image data set immediately after expiration", or "notification to the medical facility before deletion from the image storage apparatus in the image storage center".

Figure 4:
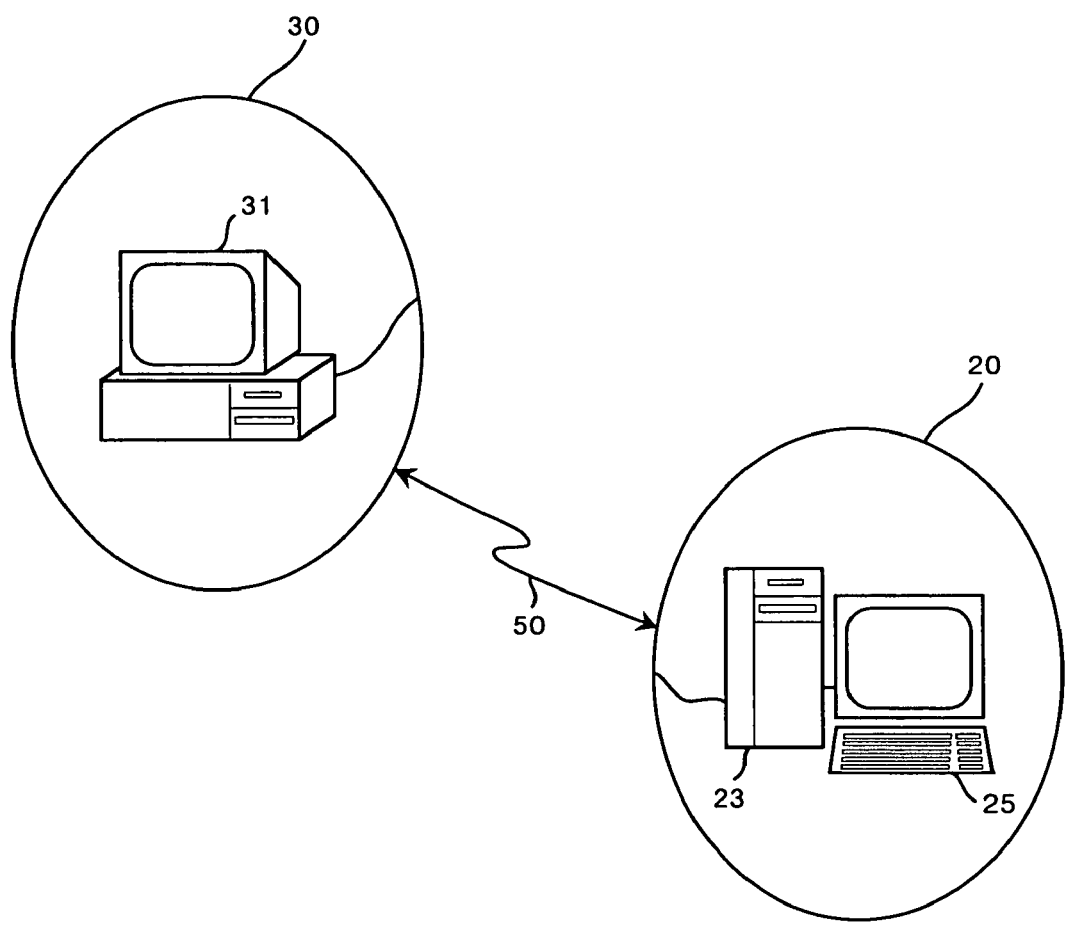
FIG. 4 is a diagram showing a configuration of another embodiment of the medical image management system in the present invention.

A second embodiment of the medical image management system of the present invention will be explained next. Since a configuration of the system is almost the same as the configuration of the first embodiment shown in FIGS. 1 and 2, explanation of the same elements as in the first embodiment having the same reference numerals is omitted. FIG. 4 is a diagram showing the configuration of the second embodiment of the present invention.

In the medical image management system in this embodiment, a storage terminal 31 installed in a medical facility 30 and an image data storage apparatus 23 installed in an image storage center 20 are connected to the Internet, and image data sets and the like stored in the storage terminal 31 are directly received by the image data storage apparatus 23 via a telephone line 50.

The storage terminal 31 in the medical facility 30 comprises a modem inside and connected to the Internet via the telephone line 50.

The image storage apparatus 23 is connected to the storage terminal 31 in a state where the image data sets and the like can be received via the Internet. The image data storage apparatus 23 has functions of receiving, storing and managing the image data sets and the like in the storage terminal 31. More specifically, reception information comprising the date of reception of each of the image data sets and the like by the image data storage apparatus 23 and a name of a data reception operator is stored in a data storage unit 23a of the image data storage apparatus 23, together with the image data sets received from the storage terminal 31. A program storage unit 23b stores a program for searching the data storage unit 23a for a desired one of the image data sets and the like, a program for displaying a screen on an input device 25, a program for calculating the date of storage expiration for each of the image data sets in the data storage unit 23a, and a program for recording the reception information at the time of data reception. It is preferable for the program storage unit 23b to store a program for regularly monitoring a storage status of the storage terminal 31 connected to the image data storage apparatus 23 via the Internet. In other words, the program storage unit 23b preferably stores a program for comparing a total amount of the image data sets in the storage terminal 31 with a capacity of a hard disc of the storage terminal 31 and for calculating free space of the hard disc.

Operation of transmission and reception of the image data sets via the Internet will be explained next.

The data reception operator in the image storage center 20 carries out storage processing on the image data sets having a predetermined amount, regularly or at the request of the medical facility 30. The operator selects data reception processing from a menu screen displayed on the input device 25 comprising the image data storage apparatus 23 in the image storage center 20, and the image data storage apparatus 23 then accesses the storage terminal 31 via the Internet. The image data storage apparatus 23 receives the image data sets and the like stored in the storage terminal 31 and stores the image data sets and the like in the data storage unit 23a. At this time, the image data storage apparatus 23 records the reception information comprising the date of reception and the name of the data reception operator, and stores the reception information.

A management operator in the image storage center 20 regularly accesses the storage terminal 31 in the medical facility 30 via the Internet, and monitors whether or not the total amount of the image data sets stored in the storage terminal 31 is going to exceed the capacity of the storage terminal. If a fact that the total amount is going to exceed the capacity as a result of regular reception is found, a countermeasure such as increasing the frequency of reception is taken.

The medical facility 30 can request output of a portion of the image data sets via the Internet from the image storage center 20 when the portion of the image data sets is necessary. Furthermore, the requested portion of the image data sets can be transferred to the medical facility 30 via the Internet.

Operation other than the above is the same as in the first embodiment.

The medical facility 30 may store the image data sets and the like in the hard disc or in any other form enabling reception of the image data sets by the storage terminal and the image data storage apparatus.

Since each of the image data sets can be identified by an image number or the like in the accompanying information, the accompanying information can be stored separately from the image data sets as long as the image data storage apparatus 23 and the storage terminal 31 can receive the accompanying information.

The image data may be stored in the hard disc of the mobile storage system 10. Alternatively, the mobile storage system 10 may have a database for the medical facility and store the image data sets therein.

The reception information may be stored separately from the image data sets if it is identified which of the image data sets the reception information corresponds to.

The date of storage expiration may be calculated by the image data storage apparatus 23 or may be recorded in the accompanying information of each of the image data sets by the medical facility 30, for example.

When the mobile storage system 10 and the image data storage apparatus 23 receive the image data sets from the storage terminal 31, only the image data sets stored after the most recent reception date of storage data may be judged and received by referring to the data of storage of each of the image data sets in the storage terminal 31.

The storage terminal 31 can store the image data sets that are stored in the image storage center 20 (such as images obtained by photographing patients) and the image data sets to be stored in the medical facility 30 for frequent reference (such as images used for examinations and researches and an image for testing an apparatus) in a state where the two types of image data sets can be distinguished. For example, the accompanying information may have a flag indicating storage in the image storage center 20. Alternatively, image identification information for identifying the images may include information for identifying the type of the image data sets. For example, the image identification information of the image data sets to be stored in the image storage center 20 may start with "A", and otherwise the image identification information starts with "B". In this case, the mobile storage system 10 for receiving the image data sets from the medical facility 30 refers to the flag or the image identification information, and receives only the image data sets to be stored in the image storage center 20 from the storage terminal 31.

The medical facility 30 preferably stores all the image data sets stored in the image storage center 20 by recording the image data sets in a separate recording medium or the like. In this manner, the medical image data sets are stored in the image storage center 20 and in the medical facility 30. Therefore, for the responsibility for restoring the image data sets whose storage is mandatory in the case of destruction, the medical facility can guarantee secure storage of the image data sets even in the case of disaster such as fire.

The image data sets may be received in the above manner or may be recorded in a recording medium brought to the image storage center 20. Alternatively, image transmission by using ISDN or the like is also possible. The medical facility 30 can select from these methods depending on the budget. Furthermore, not only the public communications network such as the Internet or ISDN but also a dedicated line or LAN in a large-scale hospital or wireless communication can be used, for example.

What is claimed is:

1. A medical image management system comprising:
   a portable image data reception device, which is connectable to medical image data storage means installed in a medical facility, having a function of receiving medical image data sets stored in the medical image data storage means from the medical image data storage means and a function of storing the medical image data sets; and
   an image data storage apparatus, which is connectable to the portable image data reception device, having a function of receiving the medical image data sets transmitted from the portable image data reception device and function of storing the image data sets, wherein
   each of the medical image data sets received by the image data storage apparatus includes accompanying information;
   the image data storage apparatus determines a storage expiration period of each of the medical image data sets stored therein, according to the accompanying information; and
   the image data storage apparatus comprises storage period management means for managing the storage expiration period of each of the medical image data sets stored therein.

2. A medical image management system as defined in claim 1, wherein the portable image data reception device further has a function of transmitting a reception completion signal to the medical image data storage means at the time of reception completion of the medical image data sets.

3. A medical image management system as defined in claim 1, wherein the image data storage apparatus further comprises output means for outputting a desired one of the medical image data sets stored therein according to a predetermined output condition input thereto.

4. The medical image management system of claim 1, wherein the image data storage apparatus determines the storage expiration date of each of the medical image data sets by using the storage period of the medical image data set and at least one of a date of reception of the medical image data set and a date of photographing of the medical image data set.

5. The medical image management system of claim 1, wherein the medical image data sets are medical images of patients.

6. The medical image management system of claim 1, wherein each of the medical image data sets are one of X-ray images, CT images, and MR images.

7. The medical image management system as defined in claim 1, wherein the image data storage apparatus obtains a storage expiration period which is included in the accompanying information.

8. The medical image management system as defined in claim 1, wherein the image data storage apparatus obtains information about input modality of each of the medical image data sets, said information about input modality being included in the accompanying information, and determines the storage expiration period according to the input modality.

9. The medical image management system of claim 1, wherein each of the medical image data sets is a single image.

10. A medical image management system comprising medical image data storage means installed in a medical facility for storing medical image data sets and for enabling transmission of the medical image data sets, and an image data storage apparatus for enabling reception of the medical image data sets from the medical image data storage means and for storing the medical image data sets, wherein
    each of the medical image data sets received by the image data storage apparatus includes accompanying information;
    the image data storage apparatus determines a storage expiration period of each of the medical image data sets stored therein, according to the accompanying information; and
    the image data storage apparatus comprises storage period management means for managing the storage expiration period of each of the medical image data sets stored therein.

11. A medical image management system as defined in claim 10, wherein the medical image data storage means has a function of transmitting a reception request signal for requesting reception of the medical image data sets stored in the medical image data storage means, and the image data storage apparatus has a function of receiving the reception request signal.

12. A medical image management system as defined in claim 11, the medical image data storage means regularly measuring a total amount of the medical image data sets stored therein and calculating a difference between a capacity of the medical image data storage means and the total amount of the medical image data sets stored in the medical image data storage means, and transmitting the reception request signal to the image data storage apparatus when the difference becomes smaller than a predetermined value.

13. A medical image management system as defined in any one of claims 10 to 12, wherein the image data storage apparatus further has a function of transmitting a storage completion signal to the medical image data storage means at the time of storing the medical image data sets.

14. The medical image management system of claim 10, wherein the image data storage apparatus further comprises output means for outputting a desired one of the medical image data sets stored therein according to a predetermined output condition input thereto.

15. The medical image management system of claim 10, wherein the image data storage apparatus determines a storage expiration date of each of the medical image data sets stored in the image data storage apparatus.

16. The medical image management method of claim 15, wherein the storage expiration date of each of the medical image data sets is determined by using the storage period of the medical image data set.

17. The medical image management system as defined in claim 10, wherein the image data storage apparatus obtains a storage expiration period which is included in the accompanying information.

18. The medical image management system as defined in claim 10, wherein the image data storage apparatus obtains information about input modality of each of the medical image data sets, said information about input modality being included in the accompanying information, and determines the storage expiration period according to the input modality.

19. A medical image management system comprising medical image data storage means installed in a medical facility for storing medical image data sets and for enabling transmission of the medical image data sets, and an image data storage apparatus for enabling reception of the medical image data sets from the medical image data storage means and for storing the medical image data sets, wherein
the image data storage apparatus comprises storage period management means for managing a storage period of each of the medical image data sets stored therein and
the image data storage apparatus comprises means for regularly measuring a total amount of the medical image data sets stored in the medical image data storage means, for calculating a difference between a capacity of the medical image data storage means and the total amount of the medical image data sets, and for receiving the medical image data sets from the medical image data storage means when the difference becomes smaller than a predetermined value.

20. A medical image management method comprising the steps of:
storing medical image data sets in storage means installed in a medical facility;
receiving and storing the medical image data sets from the medical image data storage means by using an image data storage apparatus installed outside the medical facility; and
managing a storage expiration period of each of the medical image data sets that have been stored,
wherein each of the medical image data sets received by the image data storage apparatus includes accompanying information and
the image data storage apparatus determines the storage expiration period of each of the medical image data sets stored therein, according to the accompanying information.

21. The medical image management method of claim 20, wherein the operation of managing the storage period comprises:
determining a storage expiration date of each of the medical image data sets.

22. The medical image management method of claim 21 further comprising disposing each of the medical image data sets according to the storage expiration date of respective medical image data set in a predetermined manner.

23. The medical image management method of claim 21, wherein the storage expiration date of each of the medical image data sets is determined by at least one of a type of the medical image data set and accompanying information of the medical image data set.

24. The medical image management method of claim 21 further comprising disposing each of the medical image data sets according to the storage expiration date of respective medical image data set in a predetermined manner.

25. The medical image management method of claim 20, wherein the image data storage apparatus obtains a storage expiration period which is included in the accompanying information.

26. The medical image management method of claim 20, wherein the image data storage apparatus obtains information about input modality of each of the medical image data sets, said information about input modality being included in the accompanying information, and determines the storage expiration period according to the input modality.

27. A computer-readable recording medium storing a program to cause a computer to execute the procedures of:
receiving medical image data sets stored in medical image data storage means installed in a medical facility from the medical image data storage means, each of the medical image data sets including accompanying information;
determining a storage expiration period of each of the medical image data sets based on the accompanying information;
storing the medical image data sets for the storage expiration period for each of the medical image data sets; and
transmitting the medical image data sets that have been received and stored in an image data storage apparatus.

28. A computer-readable recording medium storing a program to cause a computer to execute the procedures of:
receiving medical image data sets from medical image data storage means, each of the medical image data sets including accompanying information;
determining a storage expiration period of each of the medical image data sets based on the accompanying information; and
managing the storage expiration period of each of the medical image data sets that have been stored.

29. A computer-readable recording medium storing a program to cause a computer to execute the procedures of:
regularly measuring total amount of medical image data sets stored in medical image data storage means;
calculating a difference between a capacity of the medical image data storage means and a total amount of the medical image data sets; and
receiving the medical image data sets from the medical image data storage means when the difference becomes smaller than a predetermined value.

30. A portable image data reception device which is connectable to medical image data storage means installed in the medical facility and an image data storage apparatus having a function of receiving medical image data sets, which are transmitted from the portable image data reception device and each of which includes accompanying information, a function of storing the image data sets, said image data storage apparatus determining a storage expiration period of each of the medical image data sets stored therein, according to the accompanying information, and comprising storage period management means for managing a storage period of each of the medical image data sets stored therein, the portable image reception device having a function of receiving the medical image data sets stored in the medical image data storage means, a function of storing the medical image data sets, and a function of transmitting the medical image data sets.

31. A computer-readable recording medium storing a program to cause a computer installed in a portable image data reception device, which is connectable to medical image data storage means installed in the medical facility and an image data storage apparatus having a function of receiving medical image data sets, which are transmitted from the portable image data reception device and each of which includes accompanying information, a function of storing the image data sets, said image data storage apparatus determining a storage expiration period of each of the medical image data sets stored therein, according to the accompanying information, and comprising storage period management means for managing a storage period of each of the medical image data sets stored therein, to execute the procedures of:
receiving the medical image data sets stored in the medical image data storage means installed in the medical facility from the medical image data storage means and storing the image data sets; and
transmitting the medical image data sets that have been received and stored to the image data storage apparatus.

* * * * *